United States Patent
Schön et al.

[11] Patent Number: 6,127,092
[45] Date of Patent: Oct. 3, 2000

[54] REACTION RESIN MIXTURES AND USE THEREOF

[75] Inventors: Lothar Schön, Neunkirchen; Wolfgang Rogler, Möhrendorf; Volker Muhrer, Fürth; Manfred Fedtke, Merseburg; Andreas Palinsky, Garbsen, all of Germany

[73] Assignee: Siemens AG, Munich, Germany

[21] Appl. No.: 09/105,375

[22] Filed: Jun. 26, 1998

[30] Foreign Application Priority Data

Jun. 30, 1997 [DE] Germany .................. 197 27 822

[51] Int. Cl.$^7$ .............. G03F 7/029; G03F 7/26; G03F 7/30
[52] U.S. Cl. .................. 430/280.1; 522/31; 522/25; 522/15; 430/269; 430/288.1; 430/270.1; 430/325; 264/401; 528/90; 528/409; 525/12; 525/23; 525/24; 526/198; 526/204; 526/209; 526/222
[58] Field of Search ................ 522/31, 25, 15; 430/280.1, 269, 288.1, 270.1, 325; 528/90, 409; 525/12, 23, 24; 526/198, 204, 289, 222; 264/401

[56] References Cited

U.S. PATENT DOCUMENTS

| | | | |
|---|---|---|---|
| 4,000,115 | 12/1976 | Jacobs | 260/47 EP |
| 4,102,687 | 7/1978 | Crivello | 96/115 R |
| 4,417,061 | 11/1983 | Crivello et al. | 549/3 |
| 4,442,197 | 4/1984 | Crivello et al. | 430/280.1 |
| 4,677,137 | 6/1987 | Bany et al. | 522/31 |
| 5,073,476 | 12/1991 | Meier et al. | 430/280.1 |
| 5,144,051 | 9/1992 | Kessel et al. | 556/64 |
| 5,437,964 | 8/1995 | Lapin et al. | 430/280.1 |
| 5,476,748 | 12/1995 | Steinmann et al. | 430/269 |
| 5,510,226 | 4/1996 | Lapin et al. | 430/269 |

FOREIGN PATENT DOCUMENTS 0 889 360A1   1/1999   European Pat. Off. .

OTHER PUBLICATIONS

"Photopolymere," VEB Deutscher Verlag für Grundstoffindustrie, Leipzig 1988, p. 105.

Crivello, J.V. et al., "Structural and Mechanistic Studies on the Photolysis of Dialkylphenacylsulfonium Salt Cationic Photoinitiators," *Macromolecules*, vol. 16 (1983), pp. 864–870.

Kikkawa, A. et al., "Cationic Polymerization of Vinyl Monomers With Latent Initiators," *Makromolekulare Chemie*, vol. 192 (1991), pp. 655–662.

*Primary Examiner*—Cynthia Hamilton
*Attorney, Agent, or Firm*—Kenyon & Kenyon

[57] ABSTRACT

Curable reaction resin mixtures which are suitable for stereolithography have the following composition:

a cationically curable monomer and/or oligomer,
an initiator with the following structure:

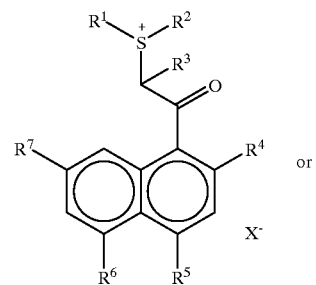

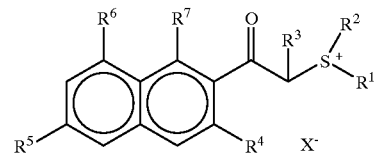

where the following applies:
$R^1$ and $R^2$ are alkyl or cycloalkyl, or together with the S atom they form a heterocyclic ring,
$R^3$ is H or alkyl,
$R^4$, $R^5$, $R^6$ and $R^7$ are H, alkyl or alkoxy,
$X^-$ is a non-nucleophilic anion,
and optionally a filler, pigment and/or additive.

19 Claims, No Drawings

REACTION RESIN MIXTURES AND USE THEREOF

FIELD OF THE INVENTION

The invention relates to curable reaction resin mixtures, in particular for production of three-dimensional plastic models by stereolithography, and use thereof.

BACKGROUND OF THE INVENTION

Stereolithography is a method of rapid prototyping engineering (RPE) with which any complex plastic models can be produced rapidly with the help of 3D CAD model data. In this method, a thin layer of a liquid reaction resin is exposed to a computer-controlled laser beam and cured in some areas. The (partially) cured structure on a platform is then lowered into the reaction resin which is in a container, and after coating (with fresh reaction resin), this new layer is again exposed to and cured with the laser in some areas. This yields the three-dimensional model layer by layer.

The photopolymers, i.e., the reaction resin mixtures used in this process, must meet a number of requirements, some of which are contradictory:

High reactivity, permitting solidification of the selected layer thickness at a minimal exposure energy, i.e., a high laser scan rate, which is thus crucial for short and therefore economical production times.

High green strength, i.e., adequate mechanical strength of the partially cured part formed in the photopolymer bath. This is necessary for a dimensionally accurate manufacturing process and nondestructive handling until postcuring of the part.

Minimal shrinkage during curing, which means minimal curl during the manufacturing process and thus optimal dimensional accuracy. Linear shrinkage in the horizontal direction is critical for low curl, because due to the layer-by-layer manufacturing process, a partially cured layer is always linked to a newly formed layer approx. 100 $\mu$m thick. Due to the reaction shrinkage of the newly generated layer, a tension is exerted on the partially hardened layers underneath, leading to distortion and the familiar curl phenomena.

Good mechanical properties of the cured parts, thus permitting function tests on the parts and the subsequent processes conventionally performed in RPE technology.

Low viscosity of <1500 mPa·s at 25° C., which is a prerequisite for optimal recoating, i.e., for short waiting times until planarization of the photopolymer layers after the layer production process.

On the basis of this complex spectrum of requirements for stereolithography photopolymers, most known resin mixtures are composed of several components. The most reactive photopolymers for stereolithography at the present time are mixtures of acrylate functional compounds which react as part of a free-radical polymerization. However, a disadvantage of this chemical basis is a relatively high reaction volume shrinkage, which leads to deformation and deviations in dimensions. Therefore, with acrylates it is impossible to achieve a balanced level of mechanical properties of engineering thermoplastics from the standpoint of high strength and high elongation at tear; instead, relatively brittle molded materials are generally obtained. Furthermore, low molecular-weight acrylates such as those used to reduce viscosity are objectionable from the standpoint of occupational hygiene.

Epoxy resins are a definite improvement with regard to mechanical properties and shrinkage. They can be cured by UV-initiated cationic polymerization. The curing rate in cationic polymerization of epoxy resins is lower in comparison with that of free-radical polymerization of acrylates, and curing requires a higher UV dose, so mixed systems of epoxy resins and a class of quick-curing compounds are generally used. For example, International Patent Application No. 92/20014 discloses cationically curable mixtures of vinyl ethers and epoxy resins, and European Patent Application No. 605,361 A2 discloses mixtures of acrylates and epoxy resins for stereolithography.

For compensation of the reduced reaction rate of cationically curable photopolymers, it is desirable to use the most powerful possible UV lasers. These are available, for example, with argon ion lasers (with wavelengths of 351 and 364 nm) and with frequency-tripled Nd:YAG lasers (with a wavelength of 351 nm), but the triarylsulfonium salts (with non-nucleophilic anions such as hexafluoroantimonate and hexafluorophosphate) that are usually used for initiation of cationic polymerization absorb to an adequate extent only in the wavelength range up to approximately 340 nm. Light of a longer wavelength, however, is not absorbed effectively and thus cannot be used in practice for initiating a curing reaction.

In stereolithography it is often desirable to intentionally leave unexposed areas in the plastic model through special exposure strategies or to keep the conversion of functional groups in the exposed areas during laser exposure relatively low. This may be expedient to minimize shrinkage effects or to save on exposure time and in this way permit more economical production of the models, i.e., by shortening production time. In these cases, however, these areas must be cured in a subsequent process. However, subsequent exposure of the finished model with UV light is not effective. For rapid laser curing of the thin layers, high concentrations of UV-absorbing initiators must be used, which also leads to absorption of light in the layers near the surface in the finished part; therefore, deeper areas are not accessible to UV postcuring. A lower initiator content or a lower optical density would also result in curing in deeper areas than desired and thus would cause inferior dimensional stability of the parts. However, thermal postcuring of unexposed areas is impossible, because triarylsulfonium salts have a high thermal stability. An increase in temperature simultaneously with or following UV exposure does accelerate the curing reaction and cause the reaction conversion to be complete, but these effects are observed only in those areas where cations were formed from the initiator in the preceding UV process. All other areas remain liquid with no change.

There is also a demand for cationically polymerizable reaction resins that are stable in storage in application areas where thicker layers must be produced, even when light-scattering or light-absorbing additives such as fillers, pigments and coloring agents are present in the mixture. Then the light is absorbed or scattered to a very great extent in the layer areas near the surface, so that the light transmitted into deeper layers is not sufficient to induce adequate curing.

Furthermore, UV curing is impossible when there are areas due to the process that are not accessible to direct exposure. In gluing together non-transparent joining parts as well as electronic components and assemblies, the adhesive is applied first and then the component is placed on it. By exposing to UV light, only the edge areas where adhesive pours out can be cured, but curing underneath the component must be induced by an additional process, e.g., thermally. The situation is comparable when components and assemblies are provided with a protective coating to protect them from ambient influences. Because of capillary forces, the lacquer migrates below the components, where again it cannot be cured by laser exposure.

It is known from U.S. Pat. No. 4,417,061 that phenacylsulfonium salts can induce cationic polymerization under the effect of UV exposure. However, it is also known that this is effectively possible only up to a wavelength of 330 nm (see Photopolymere [Photopolymers], VEB Deutscher Verlag für Grundstoffindustrie, Leipzig 1988, page 105); sensitizers must be used in the longer wavelength range. For example, it is known from U.S. Pat. No. 4,442,197 that dialkylphenacylsulfonium salts can be sensitized with aromatic hydrocarbons in particular. In addition, it is known that dialkylphenacyl compounds—together with reducing agents—can induce cationic polymerization at high temperatures. Dialkylphenacyl compounds of this type, however, have a low solubility in the cationically polymerizable reaction resin mixtures used industrially and crystallize out again over a period of time. These compounds thus cannot be used in practice if the mixtures must remain stable over a long period of time.

It is also known that electron shifting substituents in para position accelerate photolysis of dialkylphenacylsulfonium salts by stabilizing cationic intermediates (*Macromolecules*, vol. 16 (1983), pages 864–870). This corresponds to findings according to which the thermal reactivity of 4-methoxybenzylthiolanium hexafluoroantimonate is much higher than that of the unsubstituted compound (*Makromolekulare Chemie* [Macromolecular Chemistry], vol. 192 (1991), pages 655–662); specifically, effective cationic polymerization of styrene is observed starting at temperatures as low as approximately 40° C. With such mixtures, however, the viscosity cannot be expected to remain constant for weeks at room temperature.

SUMMARY OF THE INVENTION

The object of this invention is to provide reaction resin mixtures that are stable in storage and can be cured by UV and thermally by a cationic mechanism, which can be initiated with UV light in the wavelength range from approx. 350 to 400 nm, e.g., with the wavelengths of the argon-ion laser at 351 and 364 nm, and can also be cured thermally, namely by a subsequent heat treatment, in volume elements that have not been previously exposed to UV in particular.

This is achieved according to this invention by reaction resin mixtures with the following composition:

a cationically curable monomer and/or oligomer (component A), an initiator with the following structure:

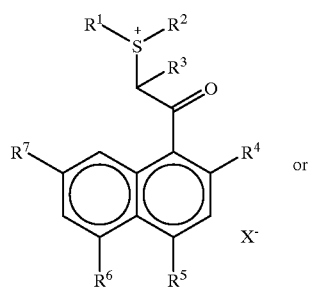

(1)

or

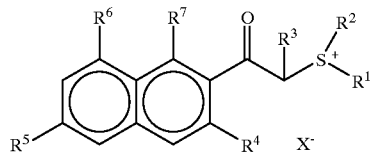

(2)

where the following applies:

$R^1$ and $R^2$ denote, independently of one another, an alkyl with one to nine carbons (linear or branched) or a cycloalkyl with four to nine carbons or together they may form a divalent aliphatic group with four to seven carbons, i.e., together with the S atom they may form a heterocyclic ring, $R^3$ is H or an alkyl with one to nine carbons (linear or branched), $R^4$, $R^5$, $R^6$ and $R^7$, independently of each other, denote H an alkyl or alkoxy, each with one to nine carbons (linear or branched), where at least one of the $R^4$ to $R^7$ groups is an alkyl or alkoxy, $X^-$ is a non-nucleophilic anion such as hexafluoroantimonate ($SbF_6^-$), hexafluoroarsenate ($AsF_6^-$) and hexafluorophosphate ($PF_6^-$), tetraphenyl borate ($B(C_6H_5)_4^-$), tetra(perfluorophenyl) borate ($B(C_6F_5)_4^-$) or trifluoromethanesulfonate ($CF_3-SO_3^{31}$), plus optionally filler, pigment and/or additive.

It has surprisingly been found that cationically curable reaction resin mixtures meet the above requirements when they contain a compound of the aforementioned structure as an initiator. Such reaction resin mixtures are stable in storage and they can be cured by UV light, in particular by laser exposure in the wavelength range of 350 to 400 nm, and also (in the unexposed areas) by merely increasing the temperature.

In general, the cationically curable monomers or oligomers (component A) may be cationically polymerizable compounds, i.e., compounds that are cationically curable. Such compounds are disclosed, for example, in European Patent Specification 126,712 B1. The monomers or oligomers may also be used in mixtures.

DETAILED DESCRIPTION OF THE INVENTION

Component A is preferably an epoxy or vinyl ether functional compound. Suitable epoxy functional compounds include, in particular, epoxidized terpenes or α-alkenes, cycloaliphatic epoxy resins, epoxy alcohols, glycidyl ethers and epoxy functionalized silicones. Cycloaliphatic epoxy resins have proven especially advantageous. Compounds with two or more epoxy groups per molecule are preferred.

Essentially all vinyl ether functionalized hydroxyl compounds may be used as the vinyl ether functional compounds. Suitable compounds include in particular cyclohexanedimethyloldivinyl ether, triethylene glycol divinyl ether, butanediol divinyl ether, bis(4-vinyloxybutyl) isophthalate, bis(4-vinyloxybutyl) succinate, bis(4-vinyloxymethylcyclohexylmethyl) glutarate and hydroxybutylmonovinyl ether or vinyl ether-functionalized hydroxypolyurethanes with aliphatic or aromatic basic structure. Vinyl ethers with two or more vinyl ether groups per molecule are preferred.

The reaction resin mixtures may also contain compounds having hydroxyl groups, i.e., polyfunctional hydroxyl compounds which play a role in the cationic reaction mechanism as part of a chain transfer reaction.

Such compounds include in particular polyalkylene polyols, polyoxyalkylene polyols and cycloaliphatic hydroxyl compounds; polyfunctional hydroxyl compounds with two or more hydroxyl groups per molecule are preferred. Using compounds that contain hydroxyl groups has proven advantageous to increase reactivity and conversion and to elasticize the resulting molded materials.

The initiators have structure (1) or (2) given above. Preferred compounds of structure (1) are those wherein $R^1$ and $R^2$ are methyl or together form an aliphatic group with four carbons, and $R^4$ and/or $R^5$ is/are a methoxy group. The initiator content in the reaction resin mixture is advantageously approx. 0.01 to 10 wt %, based on component A.

The initiators can be synthesized, for example, by reacting the corresponding thio ethers with an alkyl halide. Alkyl bromides are more reactive starting materials than alkyl chlorides because of the greater polarizability of the bromine atom and the resulting easier release of bromine. The reaction, i.e., alkylation, may be carried out in aprotic solvents as well as polar protic solvents. Due to their good solvatability, polar protic solvents stabilize the ionic products formed in the reaction. The advantage of using aprotic solvents is that the products are poorly soluble due to the low solvatability, so the chemical equilibrium is shifted in the desired manner. Following alkylation, the halide is replaced by a non-nucleophilic anion.

If alkylation is performed in an aprotic solvent, then 100 mmol of the respective alkyl halide, for example, is reacted with an equimolar amount of thio ether in 50 mL acetone, and next the mixture is stirred for one hour at room temperature. After about 24 hours, the precipitate is filtered with suction, washed with cold acetone and dried in vacuo.

To carry out the anion exchange, the sulfonium halide is dissolved in the smallest possible amount of methanol, depending on its solubility, and mixed with an equimolar amount of sodium hexafluoroantimonate ($Na(SbF_6)$), which is dissolved in methanol while heating gently. The precipitate is filtered and recrystallized repeatedly in methanol or a methanol-acetone solvent mixture until the halide test with $AgNO_3$ is negative.

If the reaction is carried out in a polar protic solvent, then 50 mmol thio ether and 50 mmol alkyl halide are dissolved in 100 mL methanol, for example, and the mixture is stirred for 12 hours at room temperature. Next 60 mmol $Na(SbF_6)$ dissolved in 60 mL methanol at 40° C. is added to the reaction mixture. After 12 more hours, the precipitate is filtered and recrystallized as described above.

In addition to the cationically curable component, compounds that cure by a free radical mechanism may also be used in the reaction resin mixtures. These include in particular compounds such as acrylic and methacrylic acid esters that are present preferably up to a concentration of approximately 30 wt %, in relation to the total resin base. In this case, the reaction resin mixtures may also contain approximately 0.1 to 10 wt %, based on the free radical curing compound, of an essentially known initiator that forms free radicals under the effect of UV exposure.

To modify the processing properties and the properties of the molded material, the reaction resin mixtures may contain additives such as mineral fillers, organic fillers, dyes, pigments, stabilizers, thixotroping agents, wetting agents and adhesion promoters.

The reaction resin mixtures according to this invention can be cured thermally or by UV light. In areas shaded from light or in areas cured only partially by UV exposure (due to the process), curing can take place by increasing the temperature simultaneously with the UV exposure or in a subsequent process. The curing temperature is generally between 80° and 200° C., preferably approximately 80° to 150° C.

In principle, all conventional UV sources such as xenon, tungsten, mercury and metal halide lamps may be used for the UV exposure; furthermore, it is also possible to use UV lasers. The laser beam can be focused with the help of an optical system; UV emission may be continuous or pulsed. Use of UV light in the wavelength range of 350 to 400 nm is preferred. It is possible to cure layers of the reaction resin mixtures by UV exposure over the full surface area or to cure only locally limited areas. Curing can be locally limited by exposure through a mask. Another possibility is to expose these areas with a computer-controlled laser beam.

The cationically curable reaction resin mixtures according to this invention are suitable for coating or bonding components, in particular of electronic components and assemblies, especially when, due to the process, there are areas shaded from the light and/or the depth of penetration of the UV light is too low for complete curing. This is the case, for example, when non-transparent parts are glued; attachment can be achieved by UV exposure of the edge areas accessible to light and curing between the joining parts can also be achieved by a thermal process. Reaction resin mixtures which contain light-scattering or light-absorbing additives such as fillers, dyes, pigments and stabilizers to modify the properties of the molded materials can be cured partially or at the surface by UV exposure; complete curing is then possible by a thermal process.

The reaction resin mixtures may also serve to produce patterns. To do so, a layer of the reaction resin mixture is produced by a suitable method, and this layer is exposed through a mask or with a laser beam. The unexposed areas are then dissolved out with a suitable solvent.

The reaction resin mixtures according to this invention are preferably used for stereolithographic production of three-dimensional structures; plastic models of any desired complexity can be produced on the basis of 3D CAD data. To do so, a thin layer of the reaction resin mixture is exposed (in a container) patternwise by means of a laser and is cured in those areas corresponding to the lower partial area of the model to be produced. This yields a first layer of the three-dimensional structure. Then another thin layer of the reaction resin mixture is formed over this first layer and is exposed, i.e., cured, accordingly. This forms a second layer of the three-dimensional structure which is bonded to the first layer. These steps of the process are repeated until the three-dimensional structure has been formed completely layer by layer. To increase productivity, it is advantageous not to completely cure the individual partial layers by a high UV dose, but instead to cure only the outer contour and a gridwork in the interior, for example, or to adjust the UV dose by the laser scan rate so that solidification is achieved in the layer but complete conversion is not. In these cases, the finished model may also be cured completely in the interior following the layer-by-layer build-up and a cleaning, if necessary (after removal from the container) by a heat treatment and/or UV exposure.

The invention will now be explained in greater detail on the basis of embodiments.

Table 1 gives an overview of initiators that have the following structure and are used in the following examples:

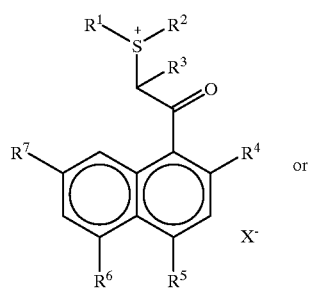

(1)

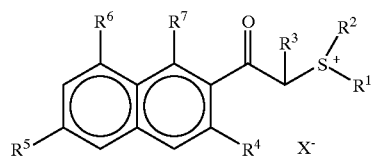

(2)

EXAMPLE 1 TO 6

To produce a resin base, equal parts by weight of bisphenol A diglycidyl ether and cyclohexanedimethyloldivinyl ether are dissolved while stirring and heating to approximately 50° C. A solution is prepared from the respective initiator and 1,2-propylene carbonate, resin base is added to this solution in an amount corresponding to the composition according to Table 2. The resulting reaction resin mixture is then stirred and homogenized at room temperature in the absence of light

EXAMPLES 7 TO 10

To prepare a resin base, 95 parts by weight bis (epoxycyclohexyl-methyl) adipate and 5 parts by weight trimethylolpropane are dissolved while stirring and heating to approximately 50° C. A solution is prepared from the

TABLE 1

| Initiator | A | B | C | D | E | F |
|---|---|---|---|---|---|---|
| Structure | 2 | 1 | 1 | 1 | 1 | 1 |
| $R^1$ | | $R^1$ and $R^2$ together form a | | | | $-CH_3$ |
| $R^2$ | | tetramethylene group $-(CH_2)_4-$ | | | | $-CH_3$ |
| $R^3$ | $-H$ | $-H$ | $-H$ | $-H$ | $-H$ | $-H$ |
| $R^4$ | $-H$ | $-H$ | $-H$ | $-OCH_3$ | $-CH_3$ | $-H$ |
| $R^5$ | $-OCH_3$ | $-CH_3$ | $-OCH_3$ | $-H$ | $-H$ | $-OCH_3$ |
| $R^6$ | $-H$ | $-H$ | $-H$ | $-H$ | $-H$ | $-H$ |
| $R^7$ | $-H$ | $-H$ | $-H$ | $-H$ | $-H$ | $-H$ |
| $X^-$ | $SbF_6^-$ | $SbF_6^-$ | $SbF_6^-$ | $SbF_6^-$ | $SbF_6^-$ | $SbF_6^-$ |
| Elementary analysis | | | | | | |
| C [%] (calculated) | 39.0 | 40.3 | 39.0 | 39.0 | 40.3 | 36.2 |
| C [%] (found) | 38.9 | 40.4 | 39.0 | 39.2 | 40.2 | 36.0 |
| H [%] (calculated) | 3.7 | 3.8 | 3.7 | 3.7 | 3.8 | 3.4 |
| H [%] (found) | 3.8 | 4.0 | 3.4 | 3.7 | 3.5 | 3.4 |
| S [%] (calculated) | 6.1 | 6.3 | 6.1 | 6.1 | 6.3 | 6.4 |
| S [%] (found) | 6.1 | 6.3 | 6.2 | 6.0 | 6.3 | 6.4 |
| Melting point (° C.) | >260 | 209 | 199–200 | 180–183 | 195 | 226–228 |

The following Examples 1 through 18 show that the reaction resin mixtures according to this invention can be cured by purely thermal means or by UV exposure. Table 2 gives the composition of the resin mixtures (in parts by weight).

respective initiator and 1,2-propylene carbonate, and resin base is added to this solution in an amount corresponding to the composition according to Table 2. The resulting reaction resin mixture is then stirred and homogenized at room temperature in the absence of light.

TABLE 2

| Example | 1 | 2 | 3 | 4 | 5 | 6 | 7 | 8 | 9 | 10 |
|---|---|---|---|---|---|---|---|---|---|---|
| Bisphenol A diglycidyl ether | 50 | 50 | 50 | 50 | 50 | 50 | — | — | — | — |
| Cyclohexanedimethyloldivinyl ether | 50 | 50 | 50 | 50 | 50 | 50 | — | — | — | — |
| Bis(epoxycyclohexylmethyl) adipate | — | — | — | — | — | — | 95 | 95 | 95 | 95 |
| Trimethylolpropane | — | — | — | — | — | — | 5 | 5 | 5 | 5 |
| 1,2-Propylene carbonate | 1.6 | 1.6 | 1.6 | 1.6 | 2.0 | 1.6 | 1.6 | 1.6 | 1.6 | 1.6 |
| Initiator A | 0.4 | — | — | — | — | — | 0.4 | — | — | — |
| Initiator B | — | 0.4 | — | — | — | — | — | 0.4 | — | — |
| Initiator C | — | — | 0.4 | — | — | — | — | — | 0.4 | — |
| Initiator D | — | — | — | 0.4 | — | — | — | — | — | 0.4 |
| Initiator E | — | — | — | — | 1.0 | — | — | — | — | — |
| Initiator F | — | — | — | — | — | 0.4 | — | — | — | 0.4 |

The results given in Table 3 show that the reaction resin mixtures according to this invention are stable in storage. Furthermore, DSC analyses have shown that these mixtures can be cured by a purely thermal mechanism. To do so, approximately 2 to 3 mg of the reaction resin mixture is weighed into a specimen container which is then sealed and heated from 25° C. to 300° C. at a heating rate of 10 K/min. The peaks are analyzed on the resulting heat flow curve. The results are also shown in Table 3.

TABLE 3

| Example | 1 | 2 | 3 | 4 | 5 | 6 | 7 | 8 | 9 | 10 |
|---|---|---|---|---|---|---|---|---|---|---|
| Stability in storage (months) (time until the viscosity doubles) | >6 | >3 | >6 | >6 | >3 | >6 | >3 | >3 | >3 | >3 |
| Results of DSC analyses (heating rate 10 K/min) | | | | | | | | | | |
| Onset (° C.) | 125 | 114 | 122 | 122 | 107 | 124 | 145 | 150 | 137 | 149 |
| Peak maximum (° C.) | 134 | 124 | 132 | 131 | 118 | 135 | 159 | 165 | 155 | 166 |
| Enthalpy (J/g) | 360 | 600 | 490 | 406 | 550 | 306 | 405 | 420 | 407 | 380 |

EXAMPLES 11 TO 16

Photocalorimetric tests have shown that the reaction resin mixtures according to this invention can be cured by UV exposure. To do so, approximately 1 mg of the reaction resin mixture is weighed into a specimen pan and then exposed to monochromatic UV light of a wavelength of 351 nm during an isothermal measurement run at 40° C. in a power differential scanning calorimeter. A peak analysis is performed on the resulting heat flow curve. The results are shown in Table 4.

TABLE 4

| Example | 11 | 12 | 13 | 14 | 15 | 16 |
|---|---|---|---|---|---|---|
| Mixture according to example no. | 2 | 3 | 5 | 6 | 8 | 10 |
| Results of photo-DSC analyses | | | | | | |
| Time until peak maximum (s) | 8.0 | 4.3 | 9.2 | 6.3 | 6.3 | 5.8 |
| Peak height (W/g) | 4.4 | 17.4 | 4.1 | 8.1 | 7.6 | 5.6 |
| Enthalpy (J/g) | 305 | 261 | 235 | 265 | 176 | 208 |

EXAMPLE 17

Printed circuit boards are provided with a protective coating by the immersion method by means of the reaction resin mixture according to Example 8 and then exposed to UVA light (50 mW/cm$^2$) for 5 minutes on both sides. All areas accessible to light are then solidified without adhesive, while resin areas below the integrated circuits are still liquid at this time. Next the printed circuit boards are heated for one hour at 125° C. The areas that are not directly accessible to UV light are then cured.

EXAMPLE 18

Rectangular areas of the resin surface of a reaction resin mixture according to Example 3 are exposed to different energy levels by means of a computer-controlled laser beam. Overlapping parallel lines spaced 0.05 mm apart are "written" on the resin surface. The laser scan rate and thus the energy applied to the surface are varied from one area to the next. Following the exposure, the cured areas are removed and cleaned in 2-propanol, then the layer thickness is measured. The results (energy applied as a function of the cured layer depth) are shown in Table 5. Laser power: 65 mW; line spacing: 0.05 mm; laser scan rate: variable from 1 to 7 m/s.

TABLE 5

| Laser scan rate | m/s | 1 | 2 | 3 | 4 | 5 | 6 | 7 |
|---|---|---|---|---|---|---|---|---|
| Energy (calculated from laser power, line spacing and laser scan rate) | mJ/cm$^2$ | 130 | 65 | 43.3 | 32.5 | 26 | 21.7 | 18.6 |
| Cured layer thickness | mm | 0.29 | 0.24 | 0.15 | 0.12 | 0.11 | 0.07 | 0.04 |

The method described here is used with photopolymers for stereolithography (determination of the working curve) to quantify their reactivity. The layer thickness is plotted as a function of the energy on a semilogarithmic scale; the point of intersection with the abscissa yields the critical exposure Ec, and the slope of the straight lines usually obtained is referred to as the penetration depth Dp. For Example 18, an Ec value of 13.0 mJ/cm$^2$ and a Dp value of 0.14 mm are obtained.

Example 18 shows that the reaction resin mixtures according to this invention can be effectively cured by selective exposure to an argon ion laser (wavelength 351 and 364 nm). The resulting values prove that these reaction resin mixtures are sufficiently reactive for use in stereolithography.

What is claimed is:

1. A curable reaction resin mixture comprising:
    a cationically curable monomer or oligomer, or a cationically curable monomer and a cationically curable oligomer (component A), and an initiator having the structure:

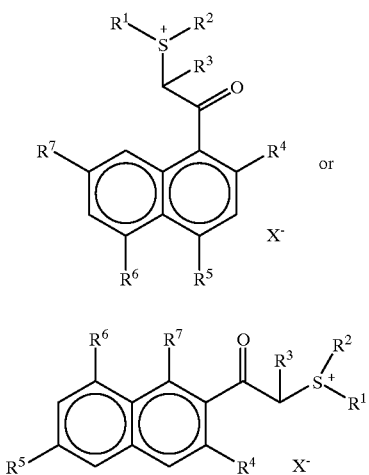

where:
R¹ and R² are an alkyl with one to nine carbons or a cycloalkyl with four to nine carbons, or together form a divalent aliphatic group with four to seven carbons,
R³ is H or an alkyl with one to nine carbons,
R⁴, R⁵, R⁶ and R⁷ are H, an alkyl with one to nine carbons or an alkoxy with one to nine carbons, with at least one of the R⁴ to R⁷ groups being an alkyl or alkoxy,
X⁻ is a non-nucleophilic anion.

2. The reaction resin mixture according to claim 1, further comprising a filler, pigment or additive.

3. The reaction resin mixture according to claim 1, wherein the initiator content is 0.01 to 10 wt %, based on component A.

4. The reaction resin mixture according to claim 3, wherein component A is an epoxy functional compound.

5. The reaction resin mixture according to claim 4, wherein the epoxy functional compound is a compound having at least two epoxy groups per molecule.

6. The reaction resin mixture according to claim 4, wherein the epoxy-functional compound is an epoxidized terpene or α-alkene, a cycloaliphatic epoxide, an epoxy alcohol, a glycidyl ether or an epoxy functionalized silicone.

7. The reaction resin mixture according to claim 1, wherein component A is an epoxy functional compound.

8. The reaction resin mixture according to claim 7, wherein the epoxy functional compound is a compound having at least two epoxy groups per molecule.

9. The reaction resin mixture according to claim 7, wherein the epoxy-functional compound is an epoxidized terpene or α-alkene, a cycloaliphatic epoxide, an epoxy alcohol, a glycidyl ether or an epoxy functionalized silicone.

10. The reaction resin mixture according to claim 1, wherein component A is a vinyl ether functional compound.

11. The reaction resin mixture according to claim 10, wherein the vinyl ether functional compound has at least two vinyl ether groups per molecule.

12. The reaction resin mixture according to claim 1, further comprising a polyfunctional hydroxyl compound.

13. The reaction resin mixture according to claim 1, further comprising a compound that cures by a free radical mechanism.

14. The reaction resin mixture according to claim 13, further comprising an initiator that forms free radicals under the effect of UV exposure.

15. A method for coating or gluing (bonding) non-transparent components, comprising the steps of
applying the reaction resin mixture as recited in claim 1 to the components,
subsequently irradiating with UV light; and
curing by a thermal treatment.

16. The method of claim 15 wherein the non-transparent components are electronic components and assemblies.

17. A method for producing structures (patterns), comprising the steps of
producing a layer from the reaction resin mixture as recited in claim 1;
exposing the layer through a mask or using a laser beam; and
dissolving out the unexposed regions using a solvent.

18. The curable reaction resin mixture of claim 1, wherein X⁻ is a non-nucleophilic anion selected from the group consisting of hexafluoroantimonate, hexafluoroarsenate, hexafluorophosphate, tetraphenyl borate, tetra (perfluorophenyl) borate, and trifluoromethane-sulfonate.

19. A method for stereolithographically producing three-dimensional structures, comprising the steps of:
a. producing a thin layer of the reaction resin mixture, as recited in claim 1;
b. irradiating the layer using a laser, on the basis of an image, a first layer of a three-dimensional structure being formed;
c. producing thin layer of the reaction resin mixture on the first layer of the three-dimensional structure;
d. irradiating the layer using a laser, on the basis of an image, a second layer of the three-dimensional structure being formed;
e. repeating the steps (c) and (d) until the three-dimensional structure is completely built up;
f. curing the complete structure by heat treatment and/or UV irradiation.

* * * * *